US006448795B1

(12) United States Patent
Ermakov et al.

(10) Patent No.: US 6,448,795 B1
(45) Date of Patent: Sep. 10, 2002

(54) THREE COIL APPARATUS FOR INDUCTIVE MEASUREMENTS OF CONDUCTANCE

(76) Inventors: Alexei Ermakov, Department of Chemistry, Rutgers University 610 Taylor Rd., Piscataway, NJ (US) 08854; Barbara Jane Hinch, 5 Parkwood Ct., Edison, NJ (US) 08837

( * ) Notice: Subject to any disclaimer, the term of this patent is extended or adjusted under 35 U.S.C. 154(b) by 0 days.

(21) Appl. No.: 09/249,691

(22) Filed: Feb. 12, 1999

(51) Int. Cl.[7] .......................... G01R 27/08; G01R 31/26
(52) U.S. Cl. ...................................... 324/724; 324/719
(58) Field of Search ................................ 324/724, 236, 324/232, 719, 750, 95

(56) References Cited

U.S. PATENT DOCUMENTS

| | | | | |
|---|---|---|---|---|
| 4,000,458 A | * | 12/1976 | Miller et al. | 324/236 |
| 4,190,799 A | * | 2/1980 | Miller et al. | 324/233 |
| 4,414,505 A | * | 11/1983 | Cuckson et al. | 324/84 |
| 4,733,182 A | * | 3/1988 | Clarke et al. | 324/527 |
| 4,795,886 A | * | 1/1989 | Carter, Jr. | 324/642 |
| 5,608,315 A | * | 3/1997 | Crayton et al. | 324/236 |
| 6,045,618 A | * | 4/2000 | Raoux et al. | 118/715 |

OTHER PUBLICATIONS

Jeanneret, et al., "Inductive Conductance Measurements in Two-Dimensional Superconducting Systems," Applied Phys. Letts. 55 (22), pp. 2336–2338 (Nov. 27, 1989).

Semiconductor Measurements and Instrumentation, edited by W. R. Runyan, McGraw Book Company (1975), on pp. 84–85.

* cited by examiner

Primary Examiner—Michael Sherry
Assistant Examiner—Jermele Hollington (57) ABSTRACT

The inventive apparatus is capable of accurate contactless sample conductance measurements. In accordance with the invention, a three coil apparatus for inductive conductance measurements comprises at least three coils, (or inductive devices,) a radio frequency (RF) generating device in conjunction with electronic circuitry for radio frequency amplitude measurement and comparison of radio frequency amplitude signals. The attainable accuracy is improved over that achieved using other conventional non-contact means by processing the differences of RF amplitude signals observed across pairs of sensing coils. Also, this invention does not require more complex RF signal processing, such as analysis of in-phase and quadrature voltage data. In a preferred embodiment, the natural resonance frequencies of the two sensing coils are tuned slightly off the RF driving frequency such that a monotonic response across a wide range of the sample's conductivity is achieved. The sensitivity of the apparatus to low sample conductances is thereby further enhanced.

16 Claims, 6 Drawing Sheets

THREE COIL APPARATUS FOR INDUCTIVE MEASUREMENTS OF CONDUCTANCE

CROSS REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

The invention pertains to an apparatus for eddy current testing of the conductance (or conductivity) or changes in the conductance (or conductivity) of a sample (such as a semiconductor wafer). The term "sample" is used throughout this specification to denote a specimen of which one intends to measure the electrical conductance.

For a variety of commercially significant purposes it is desirable to perform nondestructive tests to measure the electrical conductance, conductivity, resistance or resistivity of a sample. For example, during semiconductor product manufacturing, there is a need to measure the conductivity of various conductive thin films on semiconductor wafers and integrated circuits in a nondestructive manner.

It is well known that such measurements can be obtained by eddy current testing. One conventional apparatus for performing eddy current testing on a sample is described in U.S. Pat. No. 4,000,458 issued Dec. 28, 1976. The electrical conductivity of a lamella of conducting material (e.g., semiconductor wafers or metal films) is measured by introducing the lamella into the oscillatory magnetic field of the inductive element of the L-C tank circuit. The tank circuit is a portion of an oscillator circuit, whose driving current is adjusted, upon sample introduction, to restore the voltage amplitude of oscillation. The incremental current supplied to the tank circuit is linearly proportional to the sheet conductivity of the lamella.

Another is described in Jeanneret, et al., "Inductive Conductance Measurements in Two-Dimensional Superconducting Systems," Applied Phys. Letts. 55 (22), pp. 2336–2338 (Nov. 27, 1989). The Jeanneret, et al., apparatus employs two coils, both positioned above the sample: a drive coil, and a receiver coil. As the drive coil is driven by an AC voltage source (at a frequency of 70 kHz), the in-phase and quadrature components of the voltage at the receiver coil are measured by "conventional lock-in techniques" or by an AC mutual-inductance bridge. The resulting voltage data can be processed (with data indicating the coils' distance from the sample) to determine the sample's complex conductance.

Several techniques for conventional eddy current testing are described in Semiconductor Measurements and Instrumentation, edited by W. R. Runyan, McGraw Book Company (1975), on pages 84–85. The sensitivities of conventional techniques, however, to sheet resistivities are limited to a few k$\Omega$ and below.

We have developed an inventive apparatus for contactless measurement of sample conductances. The advantages of said apparatus, over other apparatuses described above, includes increased sensitivity, stability, and dynamic range, and decreased noise levels and thermal sensitivity. Said apparatus relies, in part, on the relative precision of RF amplitude detection. With said increased sensitivity of said apparatus, we are also not required to operate with a ferrite core (such as in Miller et al). Sufficient sensitivity for many applications is achieved with the use of "open coils." The ability to use "open coils" allows a greater flexibility and enhanced range of potential applications. In one embodiment of this invention the conductance measurement accuracy is enhanced by use of two RF amplitude detectors each producing DC signals. Thereafter the processing of only DC signals is required. Conventional contactless sample conductance measurement techniques have relied on more complex processing methods of RF signals that are inherently prone to electrical interference and noise. Said complex processing methods yield numerical values of sample sheet conductances that are less accurate than values achieved with this invention. One embodiment of the invention, detailed below, allows us to measure readily surface sheet conductances in a range from $100\Omega^{-1}$ to $10^{-5}\Omega^{-1}$.

SUMMARY OF THE INVENTION

The inventive apparatus is capable of accurate contactless sample conductance measurements. In accordance with the invention, a three coil apparatus for inductive conductance measurements comprises at least three coils, (or inductive devices,) a radio frequency (RF) generating device in conjunction with electronic circuitry for radio frequency amplitude measurement and comparison of radio frequency amplitude signals. The attainable accuracy is improved over that achieved using other conventional non-contact means by processing the differences of RF amplitude signals observed across pairs of sensing coils. Also, this invention does not require more complex RF signal processing, such as analysis of in-phase and quadrature voltage data. In a preferred embodiment, the natural resonance frequencies of the two sensing coils are tuned slightly off the RF operating frequency such that a monotonic response across a wide range of the sample's conductivity is achieved. The sensitivity of the apparatus to low sample conductances is thereby further enhanced.

BRIEF DESCRIPTION OF THE DRAWINGS

The advantages, nature and various additional features of the invention will appear more fully upon consideration of the illustrative embodiments now to be described in detail with the accompanying drawings. In the drawings.

It is understood that these drawings are for purposes of illustration of the concepts of the invention and, except for the graphs, are not to scale.

DETAILED DESCRIPTION OF THE PREFERRED EMBODIMENT

Since electrical resistivity is the inverse of electrical conductivity, determination of either of these quantities in accordance with the invention determines both of them. Although for simplicity, the invention is described herein with reference to embodiments, which determine a sample's electrical sheet conductance, it will be apparent to those of ordinary skill in the art how to implement variations on these embodiments to determine electrical sheet resistance in accordance with the invention. It will also be apparent to those of ordinary skill in the art how to implement variations on these embodiments to determine values for bulk conductivity, resistivity, sheet conductance, or sheet resistance. For example, electrical conductivity can be determined by measuring electrical sheet conductance using the described apparatus, independently measuring the linear dimension of the sample or conducting film thickness by any conventional means, and dividing the measured sheet conductance by the measured linear dimension to determine the conductivity. In the claims and the abstract, the term "conductance" is used in a broad sense to denote conductivity, resistivity, conductance, resistance, sheet conductance, or sheet resistance.

The expressions "DC voltage" and "DC signal" are used throughout the specification, including in the claims, to denote a time-invariant voltage and time-invariant signal (respectively). The expression "AC voltage" is used throughout the specification, including in the claims, to denote a periodically time-varying voltage. The expression "RF voltage" is used throughout the specification, including in the claims, to denote an AC voltage at a frequency in excess of 1 MHz. The expression "close proximity" is used throughout the specification, including in the claims, to denote the relative location of at least two objects when said at least two objects do not touch and when said at least two objects are at a distance with respect to one another that is equal or smaller than the dimension of the smallest of said at least two objects. The expression "insulating" is used throughout the specification to denote a property of a media, material or sample where the conductance of said media, material or sample is sufficiently low that said media, material or sample will not affect the function of an embodiment of the invention. The word "vacuum" is used throughout the specification to denote a space devoid of all media, wherein pressures may be less than one torr, and typically in excess of $10^{-12}$ torr. In this specification "integrated circuitry" is taken to mean circuitry that is fabricated as a small piece of material holding a complex electronic circuit, designed to replace a conventional circuit of many components.

Figure 1:
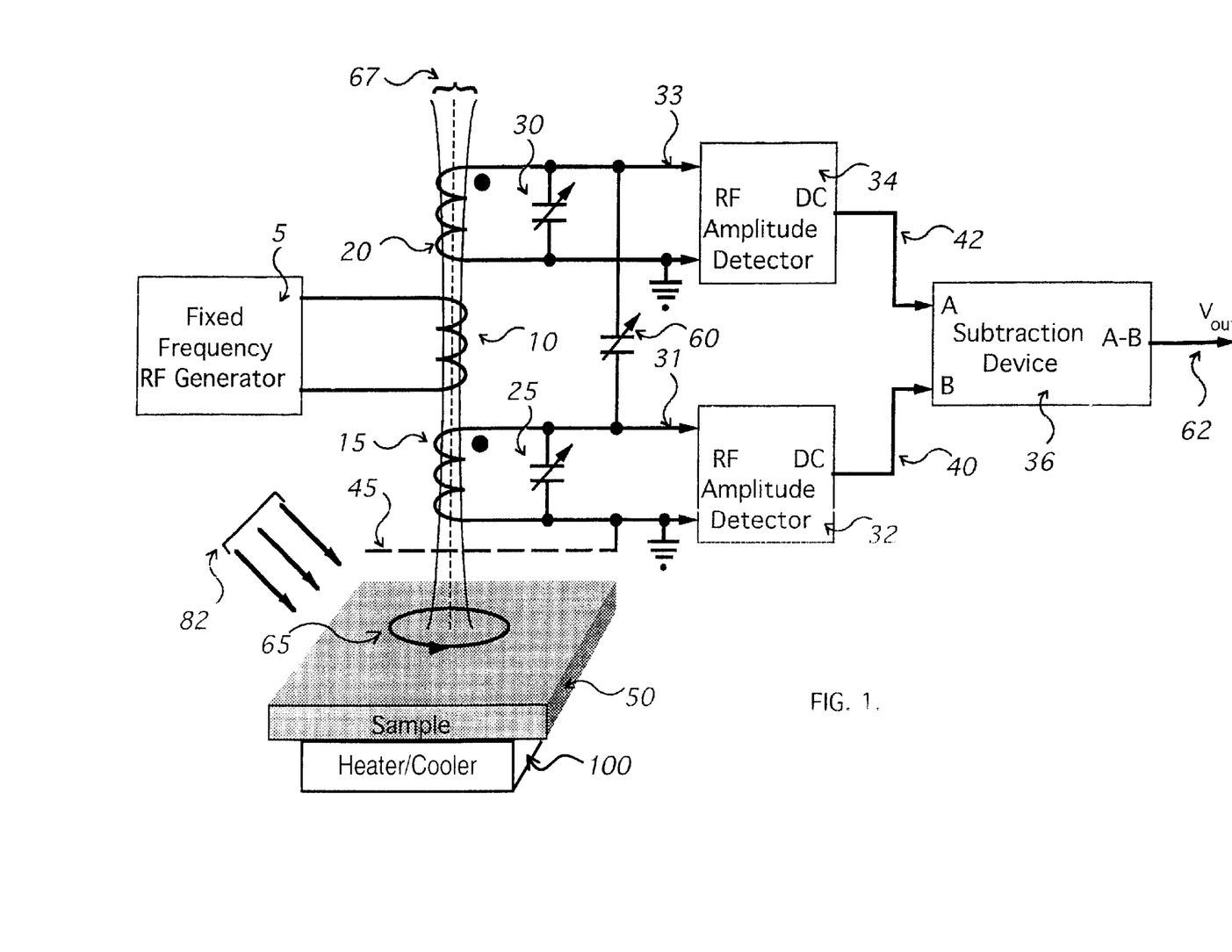
FIG. 1 is a schematic diagram of a preferred embodiment of the inventive apparatus and sample.
Figure 2:
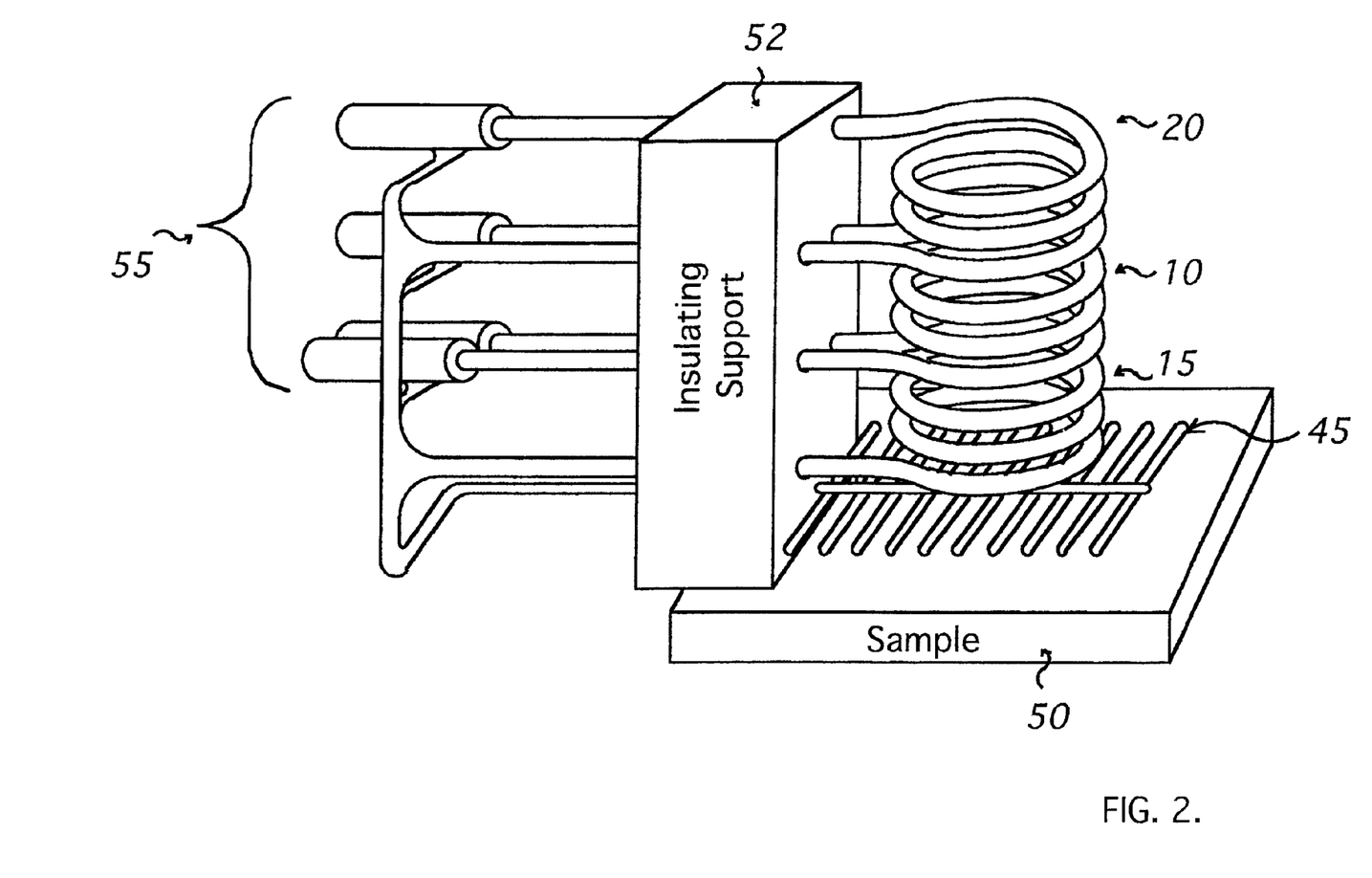
FIG. 2 is a detail picture of components of a preferred embodiment of the invention, where said components are mounted in close proximity to the sample.

A preferred embodiment of the inventive apparatus will be described with reference to FIG. 1, FIG. 2, and FIG. 3. As shown in FIG. 1, a preferred embodiment includes a fixed RF generator 5 (with a selectable operating frequency in the range from 1 MHz to 100 MHz or higher), an inductive driver means 10 (a coil), two inductive sensing means (coils 15 and 20), and capacitors (25 and 30), two RF amplitude detectors 32 and 34, a subtraction means 36 (for taking the difference between the amplitudes of the radio frequency signals 33 and 31 from the inductive sensing means 20 and 15, using two DC voltage outputs 40 and 42 from said RF amplitude detectors 32 and 34.) This preferred embodiment also includes an electrostatic shield 45 between the coils 15, 10, and 20 and the sample 50. In this embodiment the coils 15, 10, and 20, the shield 45, sample 50 and supports thereof are in a local environment comprising vacuum.

Each coil of FIG. 2 15, 10, and 20 is made of 0.5 mm diameter copper wire, comprises three full spiral turns with a pitch of 1 turn/mm. The diameters of the coils are equal at 1 cm. The coils 15, 10, and 20 are mounted coaxially, with 1 mm spacing, and held rigid with an insulating support spacer 52 made of machinable ceramic. Said support spacer 52 also holds the electrostatic shield 45 parallel to, and within 1 mm of, the base of sensing coil 15. Said shield 45 comprises a planar array of 0.25 mm diameter copper wires, with spacing 0.5 mm, which are joined such that they do not form a large conducting loop. The central wire of said planar array is grounded to the sample side of sensing coil 15. The purpose of the shield 45 is to minimize the effect of capacitive coupling between the sample 50 and the sensing coil 15 that is mounted closest to the sample 50. The coils 15, 10, and 20, support spacer 52 and shield 45 are mounted on rigid coaxially shielded supports 55.

The set of three coils 15, 10, and 20 and electrostatic shield 45 is placed parallel to the surface of sample 50. The sample 50 is in close proximity to and not in contact with the electrostatic shield 45 and the sensing coil 15. The separation between the sample 50 and the coil 15 is approximately 2 mm. The middle coil (10, driver) is electrically connected to the RF generator 5. The amplitude of the RF voltage is fixed at 1.5V, independent of the driving frequency and subsequent tuning of the sensing circuits (collectively 15, 25, 20, 30, and 60). The driver's RF electromagnetic flux induces both RF voltages in the sensing coils 15 and 20 and eddy-currents 65 in the sample 50.

Figure 3:
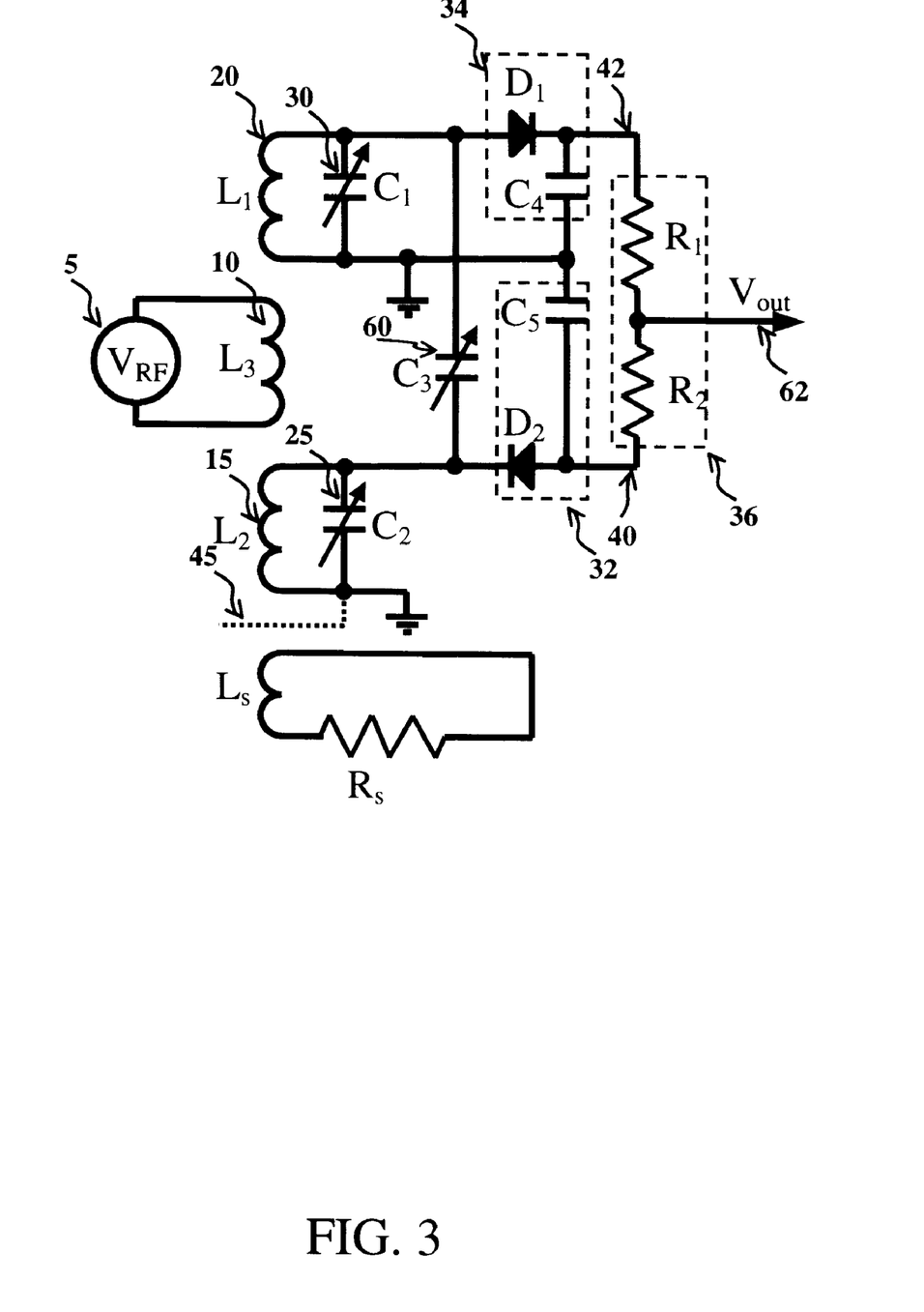
FIG. 3 is an electronic circuit diagram of an embodiment of the inventive apparatus and a sample.

The electronic circuit diagram for our contactless conductance probe is illustrated in FIG. 3. $L_3$ is the magnitude of the inductance of driver coil 10. $V_{RF}$ is the output voltage amplitude of RF generator 5. Capacitor 30, of capacitance $C_1$, is integral to, and forms a parallel resonant L-C sensing circuit with the self-inductance $L_1$ of coil 20. The capacitor 25, of capacitance $C_2$, is paired with coil 15 of inductance $L_2$. Both capacitances, $C_1$ and $C_2$, are adjustable in the range 200–800 pF. Capacitor 60, of capacitance $C_3$, couples the two L-C sensing circuits and is adjustable in the range 100 to 500 pF.

The diode, $D_1$, and the capacitor of capacitance $C_4$, constitute RF amplitude detector 34, and convert the amplitude of the induced RF voltage across the $L_1/C_1$ L-C sensing circuit to a DC signal. The diode, $D_2$, and the capacitor of capacitance $C_5$ constitute the RF amplitude detector 32 and convert the amplitude of the induced RF voltage across the $L_2/C_2$ L-C sensing circuit to an inverted DC signal. Capacitors $C_4$ and $C_5$ are 1000 pF each. $D_1$ and $D_2$ are any RF diodes.

$L_s$ and $R_s$ represent an effective inductance and an effective resistance (respectively) of sample 50. The numerical values of quantities $R_s$ and $R_s$ depend on the conductance of the sample and also on the exact dimensions of coils 15, 10, and 20, and the separation between sample 50 and sensing coil 15.

Resistors $R_1$ and $R_2$ are 100 kΩ each and constitute a subtraction device for subtraction of the amplitudes of the radio frequency signals 33 and 31 from said inductive sensing means 20 and 15 using signals 40 and 42 from the amplitude detectors 32 and 34. Strictly, (in this embodiment,) $R_1$ and $R_2$ are resistive adding circuitry operating on one positive DC amplitude signal 42 and one inverted DC amplitude signal 40. The resistors $R_1$ and $R_2$ function to provide a DC signal $V_{out}$ 62 that is proportional to the difference of amplitudes of induced RF voltages in the two parallel resonant L-C sensing circuits.

Figure 4:
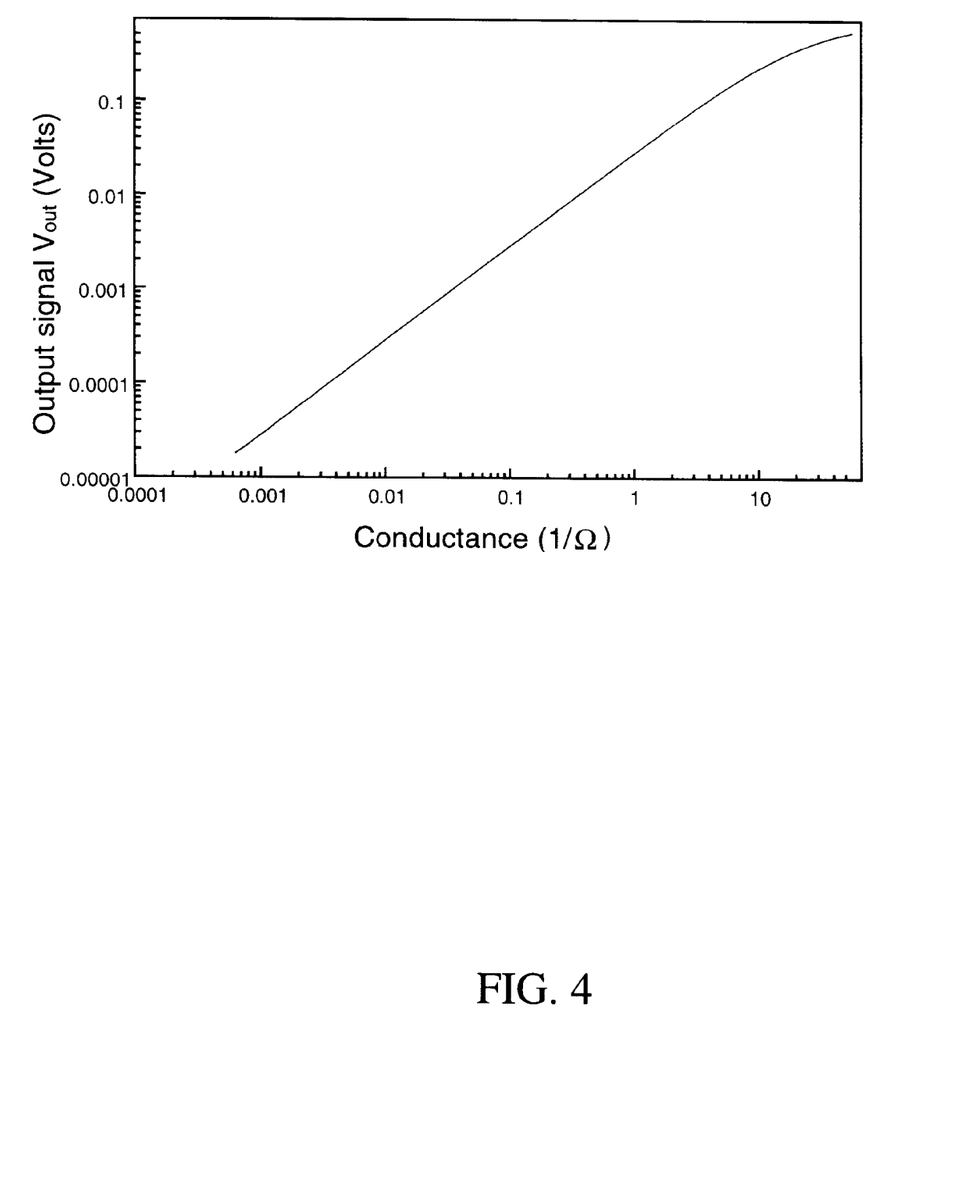
FIG. 4 illustrates a typical curve of output signal vs. surface sheet conductance change.

Eddy-currents 65 in the sample 50 are induced by the oscillatory RF magnetic field, which is produced by the driving coil 10, said field lying along flux lines 67. In low conductivity samples the magnitude of the eddy currents are proportional to the sample's conductance. Sensing coil 15, being closer to the sample than sensing coil 20, senses the presence of sample currents more strongly than sensing coil 20 and the induced RF voltages in sensing coils 15 and 20 will be affected to different extents by the sample's eddy-currents 65. Any change in the difference between RF voltage amplitudes across sensing coils 15 and 20 is proportional to a change in the sample's conductance in the low conductivity range, as illustrated in FIG. 4.

When seeking to find the absolute conductance value of a sample the probe is typically balanced in the absence of that sample such that the output, $V_{out}$ 62, is initially zero. The sample is then introduced and the ensuing $V_{out}$ 62 is proportional to the sample's conductance.

When looking for a change in a sample's conductance that may result from an external influence, (such as sample temperature variations, film growth, stress, applied magnetic fields and other causes), or that may result from variations within the sample with time, (such as crack propagation, annealing, mixing, phase segregation and other variations within the sample), the probe is initially balanced in the presence of that sample. The ensuing change in $V_{out}$ 62 is proportional to any change of that sample's conductance. The said balancing process must be achieved after all adjustments of the capacitors 25, 30, and 60 described below.

Figure 5:
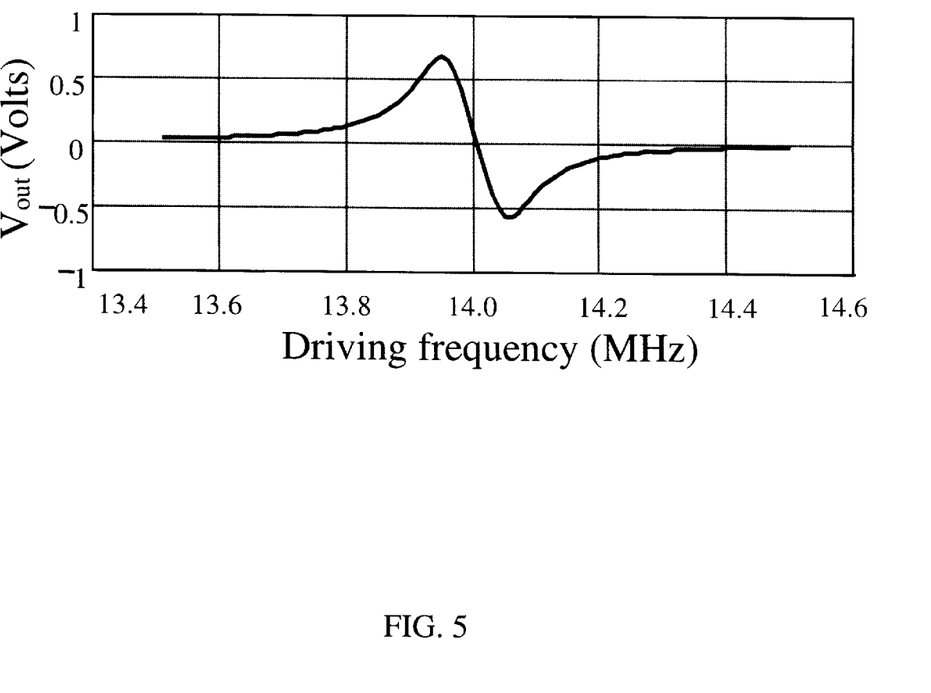
FIG. 5 illustrates a typical response curve, i.e. output signal vs. driving frequency, after tuning of the apparatus for maximum sensitivity to small sample sheet conductances.

Primarily the adjustments of the capacitances $C_1$ and $C_2$ are used to maximize the apparatus sensitivity, by operating close to resonant frequencies, and also to ensure a monotonic response for all conductivities in a wide range. For low-conductance samples the sensing circuits should be tuned, using $C_1$ and $C_2$, such that the two parallel resonant L-C sensing circuits have resonance frequencies that are slightly displaced with respect to one another. In this preferred embodiment, the resonant L-C sensing circuit containing coil 15 and capacitor 25 has a resonance at 14.1 MHz, and the circuit containing coil 20 and capacitor 30 has a resonance at 13.9 MHz. A typical test response curve $V_{out}$ 62 vs. driving frequency is shown in FIG. 5. Capacitor 60 of capacitance $C_3$ compensates for the mutual inductance between the coils 15 and 20 and is adjusted to achieve a symmetric response such that the output voltages at the maximum and minimum on graph FIG. 5 have equally positive and negative values. The output signal, $V_{out}$ can then be balanced (set to zero) by means of selecting a required operating frequency of the RF frequency generator 5 around 14 MHz (FIG. 5).

The output signal $V_{out}$ of the circuitry in this embodiment is a DC voltage. Said voltage can be measured readily by a DC voltmeter with accuracy better than $10^{-5}$V. More sophisticated measurement means may also be used, including analog to digital converters and computer assisted recording of the output signal, $V_{out}$. A typical calibration chart of our sensor is shown in FIG. 4. Absolute calibrations need be performed only at one point of the curve for accurate measurements of low sheet conductances (<$10\Omega^{-1}$).

In this embodiment of the invention, stray capacitance between sensing coil 15 and sample 50 is eliminated by electrostatic shield 45. In this manner, the monotonic response to sample conductance (FIG. 4) is maintained. In this embodiment, elimination of said stray capacitance also maintains a linear response of the apparatus to sample conductance in the limit of low sample conductances.

In this embodiment of the invention, provision is made for an external sample modification means 82, that directs chemical vapors to the sample for deposition of metal films. In this manner the sample conductance can be modified and measured in situ whilst performing deposition.

Measurement of higher sheet conductances may utilize an alternative innovative method. As shown in FIG. 4, the output signal $V_{out}$ vs. sheet conductance becomes nonlinear and saturates at high sheet conductances. To improve measurement accuracy for high-conductivity samples the following high conductance tuning method for the parallel resonant L-C sensing circuits may be applied: the output signal may be balanced, as described above, but first in the presence of a highly conductive sample surface (e.g. copper plate or superconducting material). With application of said high conductance tuning method, the output signal $V_{out}$ is now proportional to an overall sample sheet resistance for samples with high sheet conductance (>$10\Omega^{-1}$), that is samples with low sheet resistance (<$0.1\Omega$).

The preferred embodiment described here is one constructed specifically for measuring small sheet conductivity changes during in-situ thermally induced chemical vapor deposition of thin metallic films on flat semiconductor wafer material substrates under vacuum conditions. Other possible embodiments of this invention, for other specific applications, can show considerable variations in the structural design, dimensions, and coil aspect ratios, as well as electronic components.

In other embodiments of this invention, the external sample modification means 82 can include a material evaporation source, an electronic, an ionic, or a light radiation device, or a molecular beam source. The changes of sample conductance may therefore be monitored during modification of the sample where, for example, modification of the sample includes thin-film growth, electron radiation damage, ion implantation, or changes in charge carrier concentration induced by light excitation.

In other embodiments of this invention provision may be made for localized heating and localized cooling of the sample. In embodiments with said provision the sample temperature may be modified with less or no changes in temperature of the inductive means. Localized heating may for example utilize electron beam heating, direct resistive heating, or thermal contact to a resistive heater. Localized cooling may involve thermal contact to a cold sink such as a liquid cryogen reservoir, or even cooled water pipes. A heater/cooler device 100 has been indicated in FIG. 1. Said heater/cooler device may comprise a Peltier heater/cooler. In embodiments with said provision the sample temperature dependence of charge carrier densities may be deduced from conductivity measurements taken over a range of sample temperatures.

In other embodiments of this invention the local environment of said sample might not comprise vacuum. The "local environment" refers to the region or volume of homogenous composition that surrounds said sample. Said volume may be only around said sample, or may also encompass any number of the components of this invention. Said local environment may contain media including gas, solid, or liquid phases. Said media may include chemically active species. The "chemical environment of the sample" refers to the chemical composition and potential reactivity of the local environment as experienced by the sample. In all applications of this invention where local environments contain non-insulating media, said local environment must be localized around the sample alone. In other embodiments of this invention the coaxially shielded supports 55 may be omitted when the electronics are brought in close proximity to the sample; the electronic components can, for example, be brought into the vacuum when applicable.

In other embodiments the coils may be made as single turn coils, as planar spirals or in any other shape for convenience. The coils may also be enlarged or miniaturized, or the 'coils' may be constructed from differing materials, and on different supports. The coils can also be fabricated by deposition, patterning and/or growth of conductive material on platforms, said platforms made with insulating materials including polymeric, ceramic, and semiconductor materials. Some or all of the electronic components, including the frequency generator, may also be integrated on the same fabrication platform.

Figure 6:
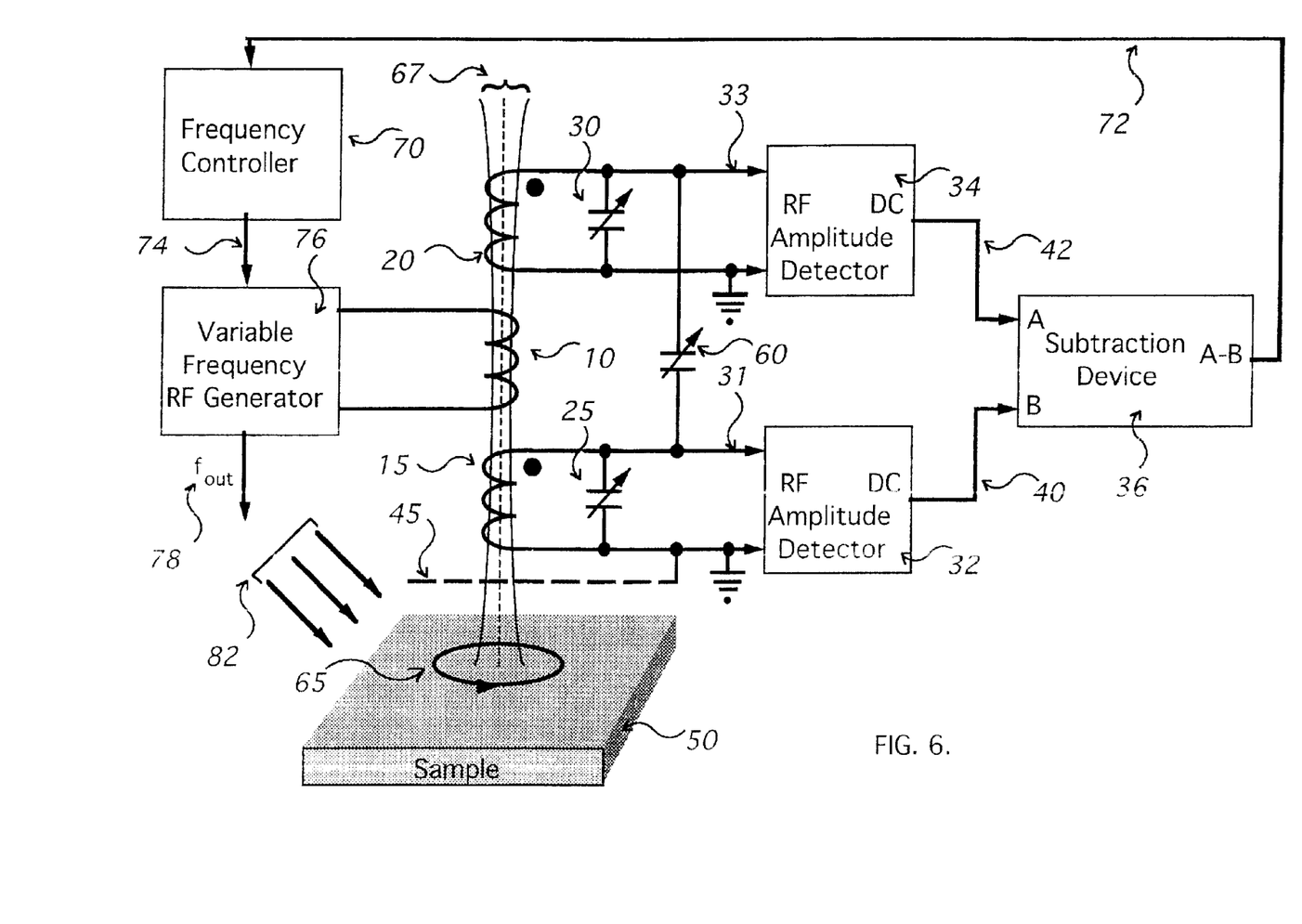
FIG. 6 is a schematic diagram of an alternative embodiment of the inventive apparatus and sample where the operating frequency of said apparatus is feedback controlled.

In other embodiments alternative measurement methods may be employed within the spirit and scope of the invention. An alternative method is illustrated in FIG. 6. In said method the RF generator is a variable frequency RF generator 76 and the operating frequency thereof is controlled by means of a frequency controller 70. The output of said frequency controller 70 and the operating frequency of said variable frequency RF generator 76 varies such that a constant (typically zero) amplitude difference signal 72 is maintained. In said alternative method the operating frequency $f_{out}$ 78 is monitored as samples are repeatedly introduced into close proximity to the coils or as a sample is modified in-situ. In said alternative method said operating frequency is a monotonic function of conductance of said samples or of changes therein. The frequency output, $f_{out}$ 78, can be used to measure and record a change in said operating frequency, a change in said operating frequency being proportional to a change in sample conductance.

In other embodiments, amplitude detectors signals 40 and 42 may take the form of digital signals and subtraction device 36 may include a computer or programmed digital processor.

In other embodiments of the inventive apparatus a placement means may be included. Said placement means may be utilized to establishing repeatable sample to sensing coil distances upon repeated introduction of a sample or samples from afar. Repeated introduction of samples, and establishing repeatable positions of these samples, is important for accurate conductivity measurements in cases where the samples and their conductances are modified ex-situ and/or in cases where accurate conductance calibration is required for measurements in comparison of more than one similar samples.

Any embodiment of this invention utilizing modified designs of the inductive means, different electronic component sizes, or other minor alterations this invention, may be used to operate at alternative resonant and driving RF frequencies. It will be apparent to those of ordinary skill in the art how to implement variations on these embodiments to increase near-surface sensitivity of electrical conductance in samples of high conductivity in accordance with the invention. It will be apparent to those of ordinary skill in the art how to implement a sequence of variations on these embodiments to extract depth-profiling information of electrical conductance in samples with spatially non-uniform electrical conductivities.

The invention being thus described, it will be obvious that the same may be varied in many ways. Such variations are not to be regarded as a departure from the spirit and the scope of the invention and all such modifications are intended to be included within the scope of the following claims.

The invention being thus described, it will be obvious that the same may be varied in many ways. Such variations are not to be regarded as a departure from the spirit and the scope of the invention and all such modifications are intended to be included within the scope of the following claims.

We claim:

1. An apparatus for measuring the electrical conductance of a sample and said apparatus comprising:
    a radio frequency generator with output at an operating frequency,
    an inductive driver means connected to said radio frequency generator,
    a pair of inductive sensing means in close proximity to said inductive driver means, one of said pair of inductive sensing means being in closer proximity to said sample than the other of said pair of inductive sensing means, and each of said pair of inductive sensing means providing a radio frequency signal,
    a pair of radio frequency amplitude detectors, each thereof connected to separate ones of said pair of inductive sensing means, and each of said pair of radio frequency amplitude detectors providing an amplitude signal,
    and a subtraction device connected to said pair of radio frequency amplitude detectors,
wherein said electrical conductance of said sample is derived from the difference of said two amplitude signals.

2. An apparatus of claim 1, wherein said inductive driver means and said inductive sensing means are incorporated in integrated circuitry that may include other electronic components contained within said apparatus.

3. An apparatus according to claim 1 wherein said sample includes semiconductor material.

4. An apparatus according to claim 1 wherein said sample includes patterned wafer material.

5. An apparatus according to claim 1 wherein said sample is being heated or cooled.

6. An apparatus according to claim 1 wherein said sample is maintained in a local environment, said local environment comprising vacuum.

7. An apparatus according to claim 1 wherein said sample is maintained in a chemical environment that is different from the chemical environment of any of said inductive driver means and said sensing inductive means.

8. An apparatus according to claim 1 wherein said electrical conductance of said sample is measured using said apparatus both before and after modification of said sample.

9. An apparatus according to claim 1 wherein said electrical conductance of said sample is measured using said apparatus during modification of said sample.

10. The apparatus according to claim 1 wherein said inductive sensing means are connected to capacitive means thereby forming resonant circuits that are tuned near said operating frequency, thereby providing near-resonance amplitude enhancement.

11. The apparatus according to claim 10 wherein said inductive sensing means are interconnected by capacitive means thereby neutralizing the mutual inductance between said inductive sensing means.

12. An apparatus according to claim 10 wherein electrostatic shielding means is utilized for improved measurement accuracy, and is electrically connected to the one of said sensing inductive means in closest proximity to said sample, and is placed between said one of said sensing inductive means and said sample.

13. An apparatus according to claim 10 wherein said amplitude signals of said amplitude detectors are DC signals.

14. An apparatus according to claim 13 wherein one of said amplitude signals of said amplitude detectors is of negative polarity and wherein said subtraction device requires only resistive adding circuitry.

15. An apparatus according to claim 13 wherein said amplitude detectors comprise diodes and capacitors.

16. An apparatus for measuring the electrical conductance of a sample and said apparatus comprising:

- a variable frequency radio frequency generator with output at an operating frequency,
- an inductive driver means connected to said radio frequency generator,
- a pair of inductive sensing means in close proximity to said inductive driver means, one of said pair of inductive sensing means being in closer proximity to said sample than the other of said pair of inductive sensing means, and each of said pair of inductive sensing means providing a radio frequency signal,
- a pair of radio frequency amplitude detectors, each thereof connected to separate ones of said pair of inductive sensing means,
- and a subtraction device connected to said pair of radio frequency amplitude detectors, and providing a differential signal proportional to the difference in amplitudes of said radio frequency signals,
- an operating frequency controller attached to said variable frequency radio frequency generator, and attached to said subtraction device, thereby maintaining said differential signal at a constant level, wherein said electrical conductance of said sample is derived from said operating frequency.

* * * * *